United States Patent [19]

Lerner

[11] Patent Number: 4,805,614
[45] Date of Patent: Feb. 21, 1989

[54] RHINITIS RELIEF DEVICE

[75] Inventor: Yaakov Lerner, Beer-Sheva, Israel

[73] Assignee: Yahav Limited, Israel

[21] Appl. No.: 69,007

[22] Filed: Jul. 1, 1987

[51] Int. Cl.⁴ .............................................. A61M 15/00
[52] U.S. Cl. ............................. 128/203.17; 128/203.27
[58] Field of Search ...................... 128/203.12, 203.16, 128/203.17, 203.26, 203.27, 204.17

[56] References Cited

U.S. PATENT DOCUMENTS

| 4,200,093 | 4/1980 | Carp | 128/203.16 X |
| 4,314,138 | 2/1982 | Itoh | 128/203.27 X |
| 4,532,088 | 7/1985 | Miller | 128/203.27 X |
| 4,604,999 | 8/1986 | Maeada | 128/203.17 X |
| 4,676,237 | 6/1987 | Wood et al. | 128/203.17 |
| 4,699,136 | 10/1987 | Krauser | 128/203.27 X |

Primary Examiner—Martin P. Schwadron
Assistant Examiner—John C. Fox
Attorney, Agent, or Firm—Lerner, David, Littenberg, Krumholz & Mentlik

[57] ABSTRACT

A device for applying a mixture of air and vapor to the nasal mucous membrane at temperatures not exceeding 47° C. comprising a water reservoir; a steam generating means within the reservoir; gas inlet means for the inlet of the gaseous medium; an outlet conduit for conducting a mixture of gas and steam away from said water reservoir, said outlet means including a first end and a second end, said first end of said outlet conduit including an outlet means for said gas stream mixture; a hollow mixing space between said gas inlet means and said second end of said outlet conduit means; a pressure-equalizing and water drainage opening connecting between said hollow mixing space and said water reservoir; and a steam outlet opening separate from said pressure-equalizing and water drainage opening and communicating with said steam generating means, positioned within said hollow mixing space and having a hydraulic diameter such as to allow outflow of steam under its own vapor pressure, whereby said steam is injected into said hollow mixing space and mixed with said gaseous medium therein and a substantially homogeneous mixture of said steam and said gaseous medium is delivered to said second end of said outlet conduit means.

7 Claims, 2 Drawing Sheets

RHINITIS RELIEF DEVICE

BACKGROUND OF THE INVENTION

1. The Field of The Invention

The present invention relates to a rhinitis-relief device employing a gaseous medium and water for treating patients suffering from rhinitis, wheter due to allergic conditions, common cold or any other factor.

2. The Prior Art

It has been known for some time that the application of a hot medium—usually air—to the nose of a patient suffering from rhinitis results in a sensible relief thereof, due both to the opening of the respiratory tracks and the sterilization thereof (Yerushalmi, A et al, Proc. Natl. Acad. Sci. USA, 79,4766-4769 (August 1982, Yerushalmi, A and Lwoff, A, C.R. Acad. Sc. Paris, t. 291 (Dec. 8, 1980)). However, in order to obtain a useful action of the hot medium and to avoid harmful effects or uncomfortable feeling during treatment, the hot medium employed must fulfill certain requirments. Throughout this specification reference will be made to air as the hot medium, for the sake of simplicity, it being understood that any other suitable gaseous medium may be employed instead of air, with the corresponding operational changes.

As stated, the hot air must fulfill certain conditions. The temperature of the air, for instance, should not exceed 47° C. in order to avoid damage to the mucous membrane of the patient's nose. Further, the humidity of the air must be as high as possible in order to avoid discomfort and feeling of dryness in the patient.

The art has, so far, provided devices which employ air heaters to obtain a stream of hot air which is then caused to vaporize water (e.g., by drawing water from a reservoir through a restriction) thereby obtaining a stream of hot humid air which is then caused to flow toward the patient's nose. The devices of the art, however, present severe drawbacks in that they are rendered expensive by the need to employ a compressor or a similar device to obtain a stream of air which is under a sufficiently high pressure to be employed for the subsequent vaporization of the water. Further, these devices are expensive in operation since they require to effect the heating of air which, as it is known to persons skilled in the art, is a relatively non-effective heat transfer process. Furthermore, the requirement for controlled conditions of the stream of hot humid air leaving the device requires to employ complex and costly control circuits to control the input of heat to the device.

Another important drawback, from the point of view of the user, is that known devices require the use of distilled (or even double-distilled) water (as required, e.g., in the "Rhinotherm" explanatory leaflet), to avoid clogging which—because of the structure of such devices—occurs easily.

SUMMARY OF THE INVENTION

It is an object of the present invention to provide a device which overcomes all the aforesaid drawbacks and which is simple in construction and operation.

It is a further object of the invention to provide such a device which is further relatively unexpensive and which does not require expensive control devices.

It is still another object of the invention to provide such a device which can use normal tap water.

The device according to the invention is characterized in that it comprises:

a. a water reservoir;
b. steam generating means comprised within the reservoir;
c. means for the inlet of a gaseous medium;
d. a conduit for the mixing of air and steam comprising at its end one or more outlets for a gas-steam mixture;
e. a hollow mixing space comprised between the inlet for the gaseous medium and the conduit for the mixing of gas and steam;
f. a pressure-equlizing and water drainage opening connecting between the hollow space and the water reservoir; and
g. a steam outlet opening from the steam generating means positioned within the hollow space whose hydraulic diameter is such as to allow outflow of steam under its own vapour pressure.

The means for the inlet of a gaseous medium preferably comprise an air blower.

The steam generating means comprise an outer encasing provided with openings for the free flow of water from the water reservoir to fill the open space within the said outer encasing, and electric heat generating and transferring means which are in contact with the water contained in the reservoir.

The conduit for the mixing of the gaseous medium and steam has a ratio a/b of its mixing legth to its diameter which is greater than about 3.

The hydraulic diameter of the outlet opening of the said steam generating means is of between 0.1 cm and 1.5 cm.

According to a preferred embodiment of the invention, the steam generating means comprise:

1. an outer encasing openening at its top into the outlet opening and provided at its bottom portion with one or more openings for the inlet of water from the water reservoir;
2. electric heat generating and transferring means for the transfer of heat to the water of the reservoir.

According to a preferred embodiment of the invention, the heat generating and transferring means comprise two parallel conducting plates.

According to another preferred embodiment of the invention, the heat generating and transferring means comprise an electric coil.

DETAILED DESCRIPTION OF PREFERRED EMBODIMENTS

Figure 1:
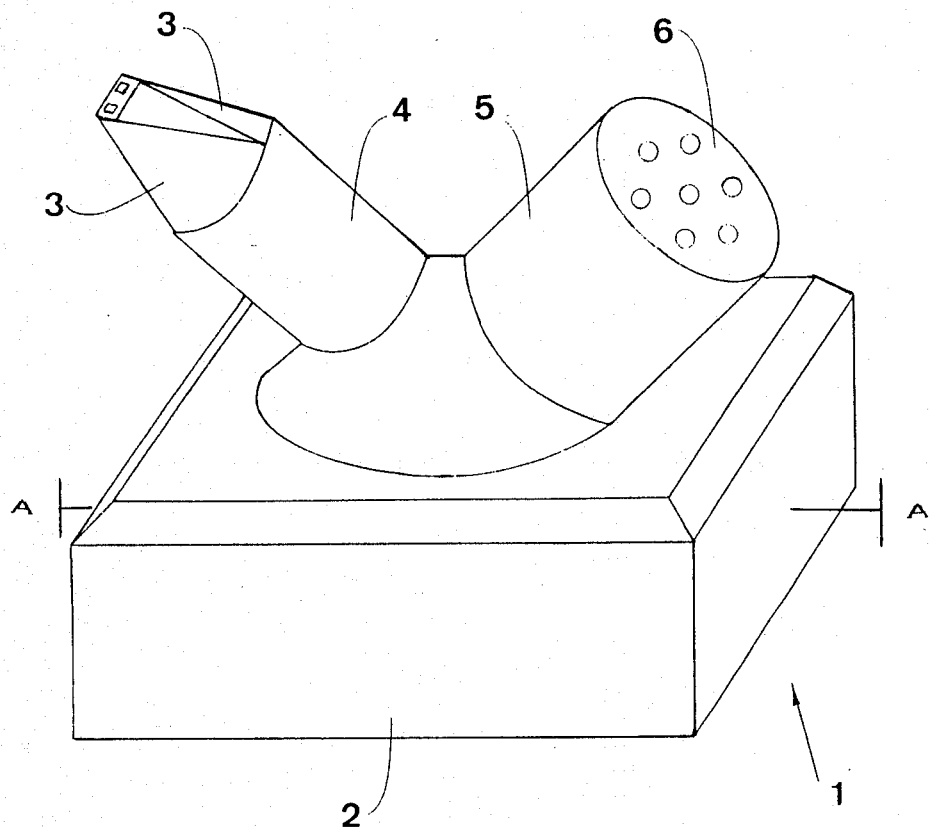
Figure 2:
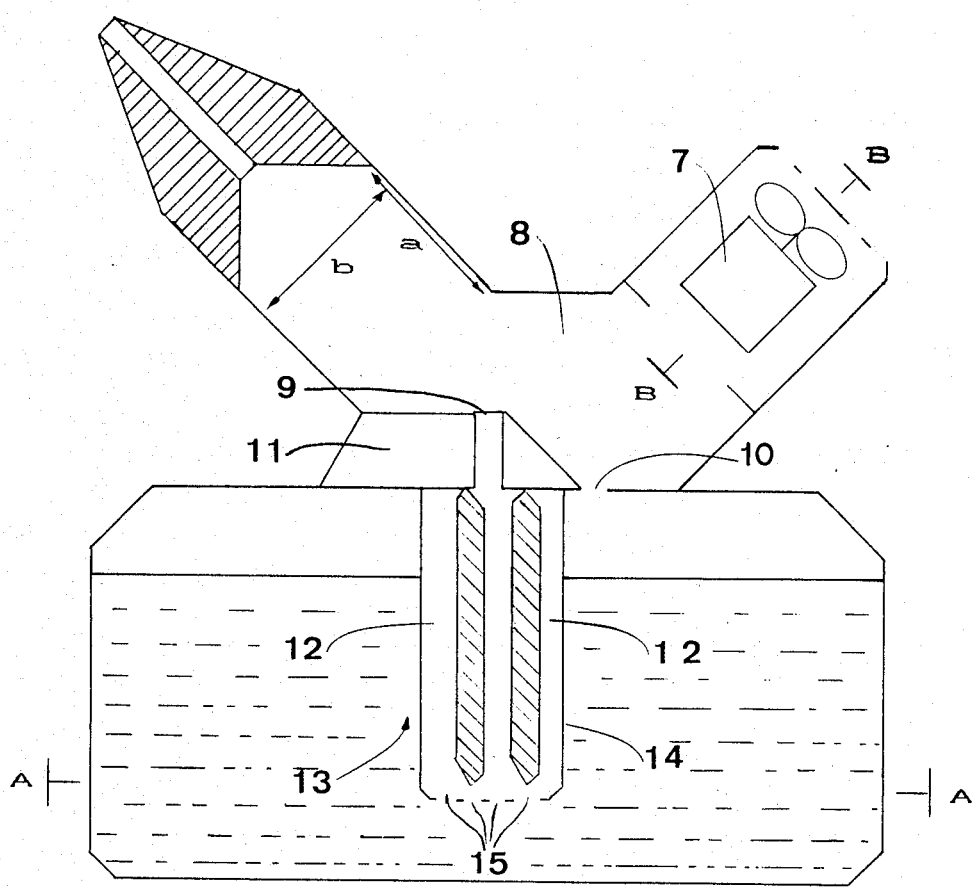

The above characteristics and advantages of the invention will be better understood from the following illustrative and non limitative description of a preferred embodiment of the invention, with reference to the appended drawings wherein:

FIG. 1 is a perspective view of the entire device; and
FIG. 2 is a cross section of the device of FIG. 1, taken along the AA axis.

With reference now to FIG. 1, numeral 1 generally indicates the device according to a preferred embodiment of the invention. The device comprises a cold water reservoir 2, two outlets 3 and 3' for directing the exiting stream of humid hot air to the patient's nose, a conduit 4, for conveying the stream to the outlets, and an encasement 5 which encases the air supply means. The encasement 5 is further provided with air inlet openings 6. The intersection angle of the axis BB of the encasement 5 with the axis AA lies within 30° to 90°.

With reference now to FIG. 2, the conduit 4 has a diameter b and a so-called "mixing length" a. These dimensions are crucial in obtaining a mixture of air and water (steam) which is homogeneous, to avoid hot spots as well as local dew formation in the stream entering the outlets 3 and 3', and leaving them to the patient's nose. The dimensions must be such that the ratio a/b > about 3. The encasement 6 houses a blower 7 which causes air to flow toward the hollow space 7 comprised between the blower 7 and the counduit 4.

A steam outlet 9, from the water reservoir 2 is positioned within the hollow space 8 which also houses a drainage opening 10 for recycling to the reservoir 2 any amount of water which condensates within the hollow space 8, and a contacts box 11 which houses the electrical contacts (not shown) for the heating plates 12 and 12' of the steam generator. The said drainage opening 10 also functions as a pressure equalizer between the hollow space 8 and the said water reservoir 2.

The steam generator, generally indicated by numeral 13, is positioned underneath the hollow space 8 and within the space defined by the reservoir 2. According to this preferred embodiment of the invention, heat is delivered to the water by two parallel plates 12 and 12'. The plates 12 and 12' are contained within a hollow containing member 14 which also comprises opening 15 for the inlet of water into the steam generator. The dimensions and number of the opening 15 must be such as to allow free flowing of water into the hollow space within steam generator 13, as it will be apparent to a person skilled in the art. According to this embodiment of the invention, the heat generating means comprise, as said, two parallel conducting plates. It is clearly understood, however, that any other suitable heat-generating means of different shape or kind may be employed to obtain the required result.

The diameter of the steam outlet 9—or the hydraulic diameter thereof when the opening is other than circular—must be such as to allow steam to flow upwards from the steam generating means under its own vapour pressure, and is preferably of between 0.1 cm and 1.5 cm.

The device according to the invention typically operates as follows. Heat is supplied to the steam generating means 13 by applying an electric tension on plates 12 and 12'. The heat is then passed to the water in the hollow space of generating means 13 by the said plates, with resulting generation of steam. The steam so generated flows upwards, due to its vapour pressure, and enters hollow space 8 through steam outlet 9. Blower 7 causes air to flow through the said hollow space 8 where a primary mixing of cold air and steam takes place, thereby heating and humidifying the inflowing air. Excess water condenses and is returned to the reservoir 2 through opening 10. Near atmospheric pressure is maintained within the reservoir 2 by the connecting opening 10. The air-steam mixture flows through conduit 4 where further homogenization of the mixture takes place, and thereafter enters openings 3 and 3' (which are directed toward the nose of the patient) from which it is discharged.

Because of the steady-state conditions at which the device is caused to operate, it is enough to provide a set point for the heat input to the steam generating device once, and then the quality of the outflowing humid air (temperature and humidity) will remain stable as long as the water reservoir is full. Therefore, no complex feedback control circuits are required for the satisfactory operation of the device.

All the aforesaid has been described for the purpose of illustration only and is not intended to be limitative. Many variations in the various means and devices of the device of the invention may be provided, without exceeding the scope of the invention.

What we claim is:

1. A Rhinitis relief device comprising:
   a. a substantially enclosed water reservoir;
   b. steam generating means within said water reservoir;
   c. gas inlet means for the inlet of a gaseous medium;
   d. outlet conduit means for conducting a mixture of gas and steam away from said water reservoir, said outlet conduit means including a first end and a second end, said first end of said outlet conduit means including an outlet means for said gas-steam mixture;
   e. a hollow mixing space between said gas inlet means and said second end of said outlet conduit means;
   f. a pressure-equalizing and water drainage opening connecting between said hollow mixing space and said water reservoir; and
   g. a steam outlet opening separate from said pressure-equalizing and water drainage opening and communicating with said steam generating means, said steam outlet opening positioned within said hollow mixing space and having a hydraulic diameter such as to allow outflow of steam under its own vapour pressure, whereby said steam is injected into said hollow mixing space and mixed with said gaseous medium therein, and a substantially homogeneous mixture of said steam and said gaseous medium is delivered to said second end of said outlet conduit means.

2. The device according to claim 1, wherein said gas inlet means comprises an air flower.

3. The device according to claim 1, wherein said steam generating means comprises an outer casing including openings for the free flow of water from said water reservoir into said outer casing, and electric heat generating and transferring means within said outer casing for heating said water contained in said reservoir.

4. The device according to claim 3, wherein said heat generating and transferring means comprises two parallel conducting plates.

5. The device according to claim 3, wherein said heat generating and transferring means comprises an electric coil.

6. The device according to claim 1, wherein said outlet conduit means has a ratio of of its length to its diameter which is greater than about 3.

7. The device according to claim 1, wherein the hydraulic diameter of said steam outlet opening is between 0.1 cm and 1.5 cm.

* * * * *

UNITED STATES PATENT AND TRADEMARK OFFICE
CERTIFICATE OF CORRECTION

PATENT NO. : 4,805,614

DATED : February 21, 1989

INVENTOR(S) : Yaakov Lerner

It is certified that error appears in the above-identified patent and that said Letters Patent is hereby corrected as shown below: Title page:

In the abstract, line 9, "stream" should read --steam--.
Column 3, line 9, "7" should read --8--.
Column 3, line 17, delete "said".
Column 4, line 44, "flower" should read --blower--.
Column 4, line 58, delete "of".

Signed and Sealed this

Twenty-second Day of August, 1989

Attest:

DONALD J. QUIGG

*Attesting Officer*    *Commissioner of Patents and Trademarks*